United States Patent [19]

Monteiro

[11] Patent Number: 5,590,169
[45] Date of Patent: Dec. 31, 1996

[54] RADIATION IMAGING SYSTEM

[76] Inventor: Sergio L. P. Monteiro, 15166F Campus Park Dr., Moorpark, Calif. 93021

[21] Appl. No.: 369,802

[22] Filed: Jan. 9, 1995

[51] Int. Cl.$^6$ ................................................. G01N 23/201
[52] U.S. Cl. .......................... 378/87; 378/146; 378/98.8; 250/370.08
[58] Field of Search .............................. 378/7, 6, 86, 87, 378/98.8, 98.9, 98.11, 98.12, 19, 146, 137; 250/370.08

[56]  References Cited

U.S. PATENT DOCUMENTS

| | | | |
|---|---|---|---|
| 4,995,107 | 2/1991 | Klingenbeck | 378/7 |
| 5,179,581 | 1/1993 | Annis et al. | 378/87 |
| 5,313,511 | 5/1994 | Annis et al. | 378/87 |

Primary Examiner—Don Wong

[57] ABSTRACT

An imaging system for medical and industrial applications that includes scanning a plurality of points of the object zone with an intermittent collimated radiation incident beam, producing a series of first digital signals representing the energy of said beam that transmits through corresponding points of the zone along the incident line, producing a series of second digital signals representing the energy of said beam scattered off the incident line by the object, storing the informational content of the first and second digital signals contents to represent an incident image array and a scattered image array, and combining the information contents of substantially corresponding points of said arrays to produce a visual image display that is more accurate than either of the first and second image arrays alone. High and low energy beams can be used and three dimensional or depth information can also be derived.

6 Claims, 2 Drawing Sheets

RADIATION IMAGING SYSTEM

FIELD OF INVENTION

The present invention relates to radiation imaging systems and more particularly to X-ray or other suitable types of such systems for use in non-destructive industrial or medical applications.

BACKGROUND

It is generally known that conventional X-ray, IR-ray, UV-ray, and other types of imaging systems experience a beam or ray scattering effect when the beam impinges upon a high density object within the object being examined. This scattering normally causes several problems including a blurring or reduction in the definition of the information in the final picture, such as the negative in a standard X-ray film.

Several attempts have been made to solve or reduce the effects of scattering problems. One such attempt includes the use of a Potter-Buck grid comprising a large number of X-ray opaque material strips interspaced by thin slices of X-ray transparent material. Although not truly a grid, the apparatus is commonly called a "Buckie-Grid" or "Buckies" in the art. Buckies function to allow most X-rays along the incident direction to penetrate to the film surface but block those scattered rays coming at an angle to the grid orientation plane.

Buckies, however, fail to solve the scattering problem because the strips fail to absorb all the scattered ray energy and they often absorb too much of the non-scattered radiation causing a picture quality degradation. Increasing radiation energy levels to compensate for the grid absorption causes other problems that require solution.

Another attempt to deal with the scattering problem appears in U.S. Pat. No. 4,342,914, issued Aug. 3, 1982 to P. J. Bjorkholm. Bjorkholm purports to disclose a system that generates signals representative of a picture using a scanning X-ray beam but Bjorkholm fails to separate the non-scattered from the scattered radiation.

ONE EXEMPLARY EMBODIMENT OF THE PRESENT INVENTION

The present invention provides a system that avoids the above mentioned problems and provides other advantages that will be understood from the following description of an exemplary embodiment which uses detected scattered radiation to create a scattered image array or matrix and which combines the same with the array or matrix of information developed from the detected incident beam transmitted through the object.

An exemplary embodiment according to the principles of the present invention comprises an X-ray or other suitable radiation frequency source that generates short (nano-second) pulses in a narrow, collimated beam, a CCD detector array mounted on a moveable support or stage, and an article or patient object secured between the source and detector. A beam steering device or mirror is movably mounted to intercept the beam and direct it along an incident line that will engage predetermined parts of the object and sweep it in a predetermined scanning pattern.

A control computer determines the center point of the detector array, determines the incident line or direction and controls the movement of the stage and the mirror so that the incident line is always directed at the center of the detector As the beam propagates through the object, it is absorbed, scattered or transmitted through without a change in direction. Transmitted rays will impinge upon the central pixels of the CCD array, scattered rays will impinge upon detector elements removed from the center pixels, and absorbed ray energy will not fall on the detector at all.

The detector elements generate separate signals representative of the energy levels of received incident and scattered rays and feed this information to the computer that digitizes and processes the information to produce two images, one negative image picture composed of information from the transmitted (incident) rays only and the other a positive image picture from the scattered ray information only. The image created with the transmitted radiation (transmitted image for short) is a negative image because the measured radiation intensity is smaller for points and line of sight of larger object density. On the other hand, the image created with the scattered radiation (scattered image for short) is a positive image because the measured radiation intensity is larger for points and line of sight of larger object density. As density increases, the transmitted energy is smaller and the scattered energy is larger. On a gray scale picture, for high density points, the transmitted image is light colored and the scattered image is dark colored.

The transmitted and scattered images can be created in the following way. The object is scanned by an X-ray beam. Each beam, momentarily stationary, pierces the object along a particular line. This line intersects the detector, placed behind the object perpendicularly to the propagation direction of the X-ray beam, at one point. This point is where the transmitted radiation is measured. The surrounding detectors measure the amount of scattered radiation. For each beam position two numbers are created: one number is the numerical value of the amount of X-ray energy in the pixel that measures the transmitted radiation, the other number is the numerical summed value of the amount of X-ray energy in the surrounding pixels around the incident direction.

After the X-ray beam is aimed at as many points on the object as the desired resolution requires, the computer has stored in memory two arrays of numbers, one array associated with the transmitted radiation intensity, the other array associated with the scattered radiation intensity.

The transmitted array can be used to create a continuous tone print such that the darkness at any point of the print is proportional to the numerical value of the number written on the corresponding number of the transmitted array. Because the number written on the transmitted array is a measurement of the transmitted beam intensity at the particular direction, and also because the transmitted beam creates a negative image, this print created as described with the transmitted array is a negative image of the object opacity.

Likewise the scattered array can be used to create a continuous tone print such that the darkness at any point of the print is proportional to the numerical value of the corresponding number written on the scattered array. And because the number written on the scattered array is a measurement of the scattered beam intensity at the particular direction, and also because the scattered beam creates a positive image, this print created as described with the scattered array is a positive image of the object opacity.

There are several conventional ways now to process these two images to get one final image. All of the conceivable ways to process these images are of such a nature that image defects from one of the two images can be corrected or at least ameliorated by the other image. One elementary way is to create a positive image from the negative transmitted image, normalize it to the same average numerical value (degree of grayness) as the scattered positive image, then take a point-by-point average of the two.

In addition, according to another aspect of the present invention, the scattered ray information also bears information related to the distance from the detector plane to the point at which scattering took place, since the distance from the center of the detecting element is proportional to the distance from the point of scattering to the detector plane along the incident line. This information can also be processed by the computer to yield a three-dimensional picture or image.

DRAWINGS

Other and further advantages and objects will become apparent with the following detailed description when taken in view of the appended drawings, in which.

It should be understood that these drawings are not drawn to scale but serve to illustrate the principles of the present invention.

DETAILED DESCRIPTION OF EXEMPLARY EMBODIMENT

Figure 1:
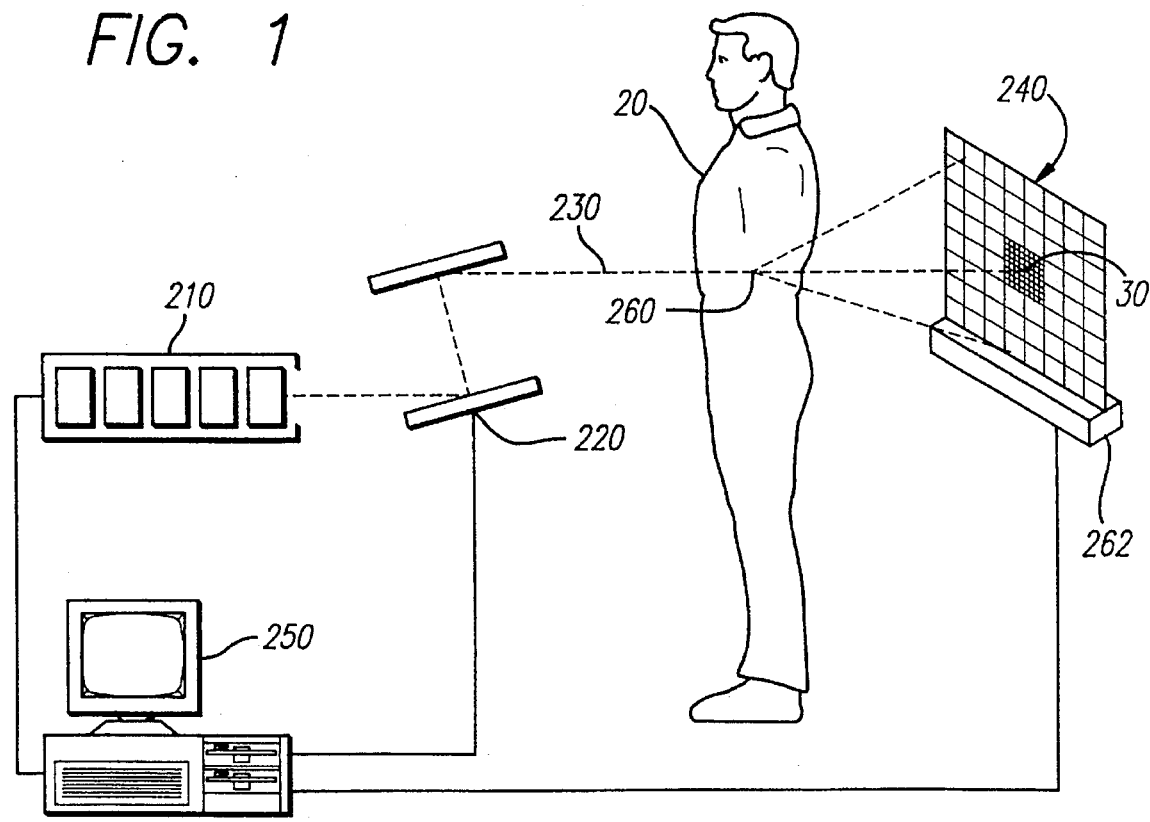
FIG. 1 is a schematic layout representation of one exemplary embodiment of a system according to principles of the present invention used in a medical application.

With reference to FIG. 1, the system comprises a source 210 of electromagnetic radiation, which could be a conventional source fitted with a pinhole, or a synchrotron radiation source with or without an insertion device (like a wiggler or an undulator), capable of producing a pulsed, well-collimated photon beam, for example, X-rays, a moveable steering assembly mirror 220, capable of redirecting said electromagnetic radiation beam towards different parts of the object 20, one or a plurality of solid-state energy detectors 240, for example, of the type generally known as charged-coupled-device (CCD). placed behind the object 20, in the same general planar orientation as the X-ray film would be positioned in prior art systems. A moving stage 262, on which said plurality of solid-state detectors is mounted, and capable of moving said plurality of solid-state detectors in such a way as to maintain the center of said plurality of solid-state detectors constantly along the direction of the propagating incoming radiation beam 230 while said incoming radiation beam 230 scans the subject 20, a plurality of electronic valves or switches (not shown) are provided to start and interrupt the measurements in each element in said solid-state detectors, as well as reset them to zero, to prepare for the next measurement. The interconnection and interaction between these main elements are described below, and each part described above is well-known in its respective field.

The electromagnetic radiation source used for the device disclosed in this patent application is preferably pulsed, with controllable pulse width and pulse repetition rates. The pulse width should be short. One embodiment described herein, the pulse width is of the order of two nanoseconds (2 ns). The pulse repetition rate should be matched to the read-out time needed for the solid-state electronic detectors 240, described below, and should be such that a new radiation pulse or wave packet is sent towards the object 20 immediately after the solid-state detector 240 finished reading the energy values originating from the previous pulse. Using current available technology this read-out time is less than 1 μs. Consequently, the electromagnetic energy source (X-ray source) should emit a 2 ns pulse at 1 μs interval. An example of the electromagnetic source is a charged particle accelerator fitted with a wiggler magnet. The radiation produced by wiggler magnets inside a charged particle accelerator is well collimated and its frequency is tunable over a wide range. A wiggler magnet will produce a short pulse of electromagnetic radiation, and the time between pulses is controllable. Accelerators and wigglers are a technique well known in the art.

One or a plurality of steering mirrors, to direct said well-collimated beams of electromagnetic radiation pulses towards object 20, are mounted on rotating/translation devices controlled by a microcomputer 250. Both the mirrors, for visible radiation, UV radiation, or X-rays, as well as the steering devices and associated microcomputer and controlling hardware and software are off-the-shelf elements, manufactured by a large number of companies, all well known by practitioners of the art of optics.

The solid-state electronic detectors 240 can be of the type generally known as charged-coupled devices (CCD), or their equivalents. Said solid-state electronic detectors are manufactured for use with electromagnetic radiation characterized by any frequency, from the infrared (IR) through the visible, ultraviolet (UV) to X-rays. These devices may be manufactured as individual detectors of arrays containing detectors on a linear arrangement or on a square grid. Typical dimensions of each detector are of the order of 25 μm or more. They are currently manufactured along a line, or inside a circular or square area. At present, these detectors are manufactured in sizes as large as roughly a few thousand detectors for the linear variety (usually in multiples of 1,024 individual detectors) and a few million detectors for the area variety.

Figure 2:
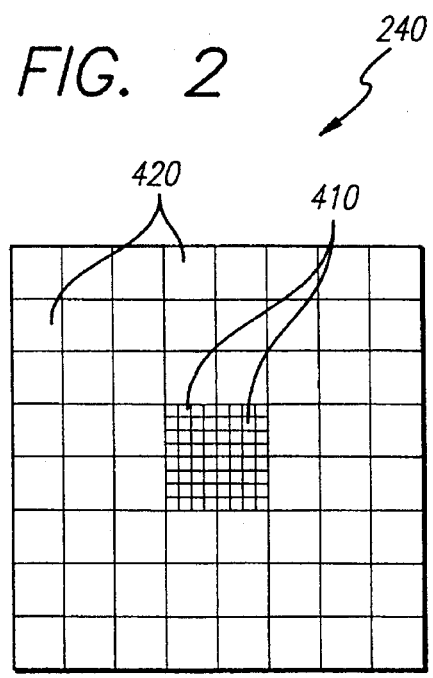
FIG. 2 is a schematic representation of an example of a CCD detector that can be used in the system of FIG. 1.

In one example of the exemplary embodiment, the detector array is made as shown in FIG. 2, that is, 64 small detectors 410 with dimensions 25 μm×25 μm, on a square array, are surrounded by 60 larger energy detectors 420 of dimensions 100 μm×100 μm (8×8 square, minus four at the center, corresponding to the area used by the smaller detectors). Not shown in FIG. 2 is that this array of 100 μm size detectors is in turn within another array of 60 larger energy detectors of dimensions 400 μm×400 μm (also arranged on an array 8×8 square, minus the four at the center, corresponding to the area used by the 100 μm energy detectors), and this array of 60 energy detectors of 400 μm in side, is in turn within a last square array of another 60 larger-sized energy detectors of dimensions 1,600 μm=1.6 mm in side, also arranged on a square of 8 energy detectors by 8 energy detectors, with the four central positions on this larger array being occupied by the 60 energy detectors of dimensions 400 μm×400 μm. The total size of the energy detector of the preferred embodiment of this invention is thus a square of side 8×1.6 mm=1.28 cm.

The actual detector size is determined by the amount of radiation scattering, which in turn depends on the photon energy or kilovoltage used and the distance from the scattering center to the detector array. These solid-state electronic energy detectors 240 are mounted in positioning stages, such as the type used in any automated optical bench, and by the semiconductor manufacturing industry to automatically and accurately position wafers and masks inside the vacuum chambers used in the production of electronic components. The needed accuracy for positioning is actually not as demanding for the present invention disclosed herein than for the semiconductor manufacturing industry; consequently, the demands on the available equipment are well within the current technology.

To each beam direction along the object, there corresponds a number which is the energy of the transmitted radiation along this particular direction. This number can be arranged, for convenience, on a two dimensional array in such a way that numbers that are above, to the left, below, etc. correspond to directions along the object that are corresponding above, to the left, below, etc. too. There will be three distinct things all associated with an object: lines along the object, numbers on a two dimensional array so arranged that their relative position follows the same relative position of the lines along the object, and lastly a gray-tone image such that the darkness of each point on it is proportional to corresponding numbers written on the two dimensional array. The transmitted array can be used to create a continuous tone print such that the darkness at any point of the print is proportional to the numerical value of the number written on the transmitted array matrix that corresponds to the point on the print. Because the number written on the transmitted array is a measurement of the transmitted beam intensity at the particular direction and also because the transmitted beam intensity decreases with increasing object density, it follows that the transmitted beam intensity creates a negative image of the object density. This print created as described with the transmitted array is a negative image of the object opacity. Thus, each entry on the matrix is associated with a point on the image, which in turn is associated with a particular direction along and through the object.

Also, to each beam direction along the object, there corresponds a number which is the energy of the scattered radiation along this particular direction. This number can be arranged, for convenience, on a two dimensional array in such a way that numbers that are above, to the left, below, etc. correspond to directions along the object that are corresponding above, to the left, below, etc. too. There will be three distinct things all associated with an object: lines along the object, numbers on a two dimensional array so arranged that their relative position follows the same relative position of the lines along the object, and lastly a gray-tone image such that the darkness of each point on it is proportional to corresponding numbers written on the two dimensional array.

The scattered array can be used to create a continuous tone print such that the darkness at any point of the print is proportional to the numerical value of the number written on the scattered array matrix that corresponds to the point on the print. Because the number written on the scattered array is a measurement of the scattered beam intensity at the particular direction and also because the scattered beam intensity increases with increasing object density, it follows that the scattered beam intensity creates a positive image of the object density. This print created as described with the scattered array is a positive image of the object opacity.

OPERATION OF ONE EMBODIMENT OF THE INVENTION

In operation, the X-ray source generates the short pulses of narrow-collimated beams, translating/rotating mirror 220 deflects the beam to sweep the object and stage 262 moves the detector array within the detector X-Y plane. Control computer 250 controls the incident line 230 and the stage movement so that line 230 is directed to point 30 at the substantial center of the detector array 240.

One embodiment of the invention disclosed in this patent application uses a wiggler magnet as a source of radiation. The radiation is to be directed towards a specific direction 230 for a short time interval which, in the preferred embodiment of this invention, is from as long as a few nanoseconds to as short as a few picoseconds. The radiation is then turned off by, say, redirecting the particle beam that produces it away from the wiggler, through another path in the accelerator. No further radiation is directed towards the object 20 until all the energy readings on all the cells of the solid-state detector array 240 are made, and their values conveniently stored in a microcomputer. Using current technologies, this can be done in a time of the order of 1 microsecond, this time depending largely on the number of individual solid-state detectors used in the array, after which time another photon beam is sent towards object 20, but along another direction. In the preferred embodiment of this invention, a course scan is made first, moving the radiation beam (and the detector always along the beam direction) with larger steps, say 100 microns. This course scan is to be followed by a fine scan, with smaller steps, say 10 microns, which produces a high resolution image. Said fine scan is to be produced for selected parts of object 20, as determined from observation of the course image produced by the course scan.

The sequence of pulses is as follows, with typical times suggested for the preferred embodiment: (1) a short burst of photons (2 ns) is directed towards object 20, (2) after 5 ns said burst of photons reaches the object 20, for example, a human being, (3) after another 1 ns burst of photons emerges on the other side of object 20, except for the ones that have been absorbed by object 20, (4) after another 0.1 ns the fraction of said burst of photons that have propagated through object 20 reaches the solid-state electronic detector 240, the non-scattered photons depositing their energy on the surrounding detectors, (5) after a comparatively long time of 1 µs all the detectors in the array have been read, the values stored in the controlling microcomputer, and the detectors themselves have been zeroed in preparation for the next cycle. This cycle generates the information on the absorption and scattering properties of object 20 along the specific direction of radiation propagation used for this cycle. The next cycle repeats this same sequence, but the photon beam is then moved to another direction, to probe the next volume of object 20, the energy detector array also moving in such a way that the center detector is still along the propagation direction of the collimated radiation beam (i.e., to determine another point in the opacity image of object 20), and so forth.

Figure 3:
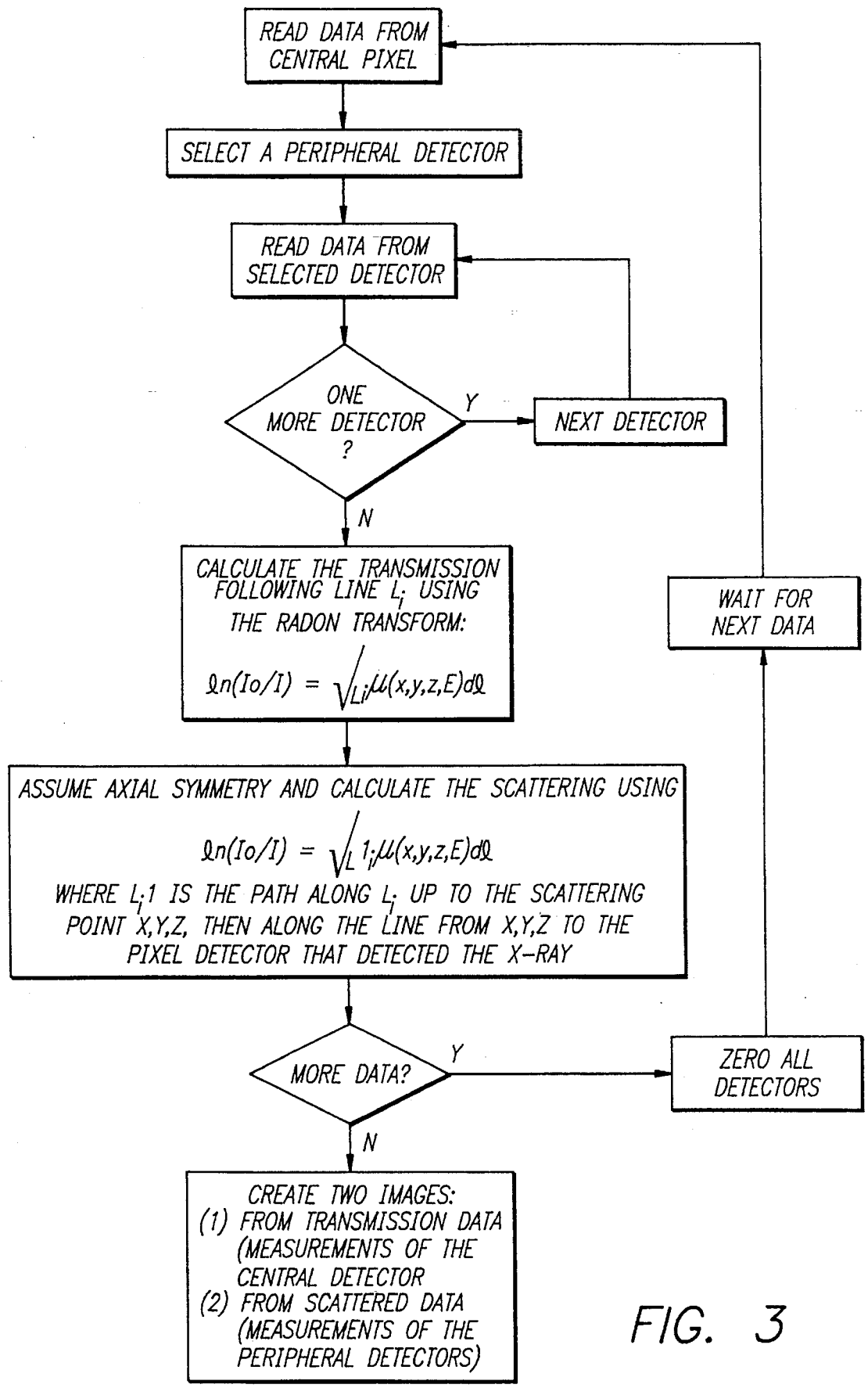
FIG. 3 is a block flow diagram of the software tasks that can be used in the system of FIG. 1.

Further detail of the software control tasks and decision tree can be seen in FIG. 3.

One example of cycle requirements is for a picture of a human arm, measuring 25 cm by 7.5 cm, or $25 \times 10^4$ µm by $7.5 \times 10^4$ µm, the area to be scanned is $1,875 \times 10^8$ µm², say roughly $2 \times 10^8$ µm². For a low-resolution picture, moving the beam and detector by 100 µm at a time, both horizontally and vertically, means that the area of each image point is $10^4$ µm². Dividing the area to be scanned ($2 \times 10^8$ µm) by the area covered by each measurement ($10^4$ µm²), one arrives at a figure of $2 \times 10^4$ points to be measured. At a frequency of MHz (T=1 µs per point, it would take a time of $$t = (10^4/10^6)s = 0.01 \ s = 10 \ ms$$

to complete one picture. During such a short time there need to be no special precautions taken to keep the patient from moving. For a higher resolution picture, 1000 dots/inch, the measuring area should be 25 µm×25 µm, and the total time needed for the above picture should be multiplied by 16, i.e., 160 ms. So, a low resolution picture of an arm takes only 10 ms, while a high resolution picture takes slightly more than one tenth of a second.

Yet another advantage of the system according to this invention includes the combination of low and high resolution for different areas of interest. Indeed, after a low resolution picture of the possible area of interest and of its surroundings, the operator will, based on the low resolution picture, determine the areas for higher resolution pictures. Only the needed areas will then be exposed to the extra X-rays for a high-resolution picture, as opposed to the full area further decreasing the radiation exposure for human subjects.

Yet another advantage of the system disclosed herein is the use of low-energy photons, or soft X-rays, which the radiologists call low kilovoltage X-rays. Low-energy photons cannot normally be used in X-ray pictures of human beings, although they are less harmful to the patient, because they suffer more scattering, thereby degrading the image quality to a point of becoming useless for the purpose of generating an X-ray picture. But because the system according to the invention uses both transmitted and scattered radiation for image formation, there is no image degradation due to scattering, and consequently a new radiological window is opened, with a consequent decrease in harmful health effects.

In addition, varying photon energy can add information about depth structure, as scattering is a known function of photon energy. Thus, an extra high resolution picture can be taken at different photon energy (different kilovoltage, in the radiologist's language), and the combination of two pictures at different photon energies can be combined to give depth information on the features shown in the picture.

Figure 4:
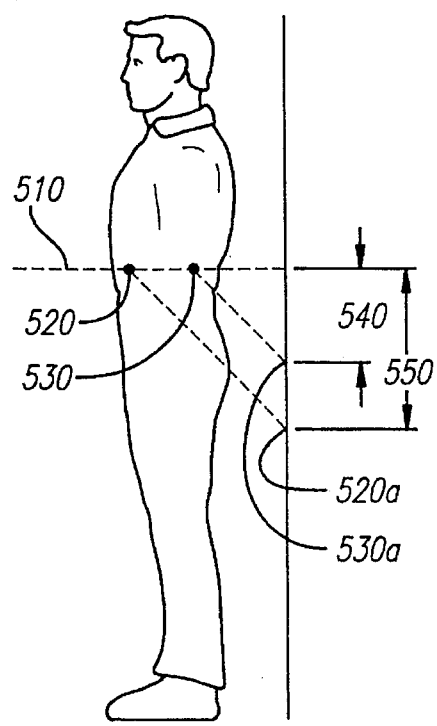
FIG. 4 is a schematic drawing showing the different results of scattering caused by scattering points located at two different positions along the incident beam direction.

Depth information can also be achieved because the angular scattering cross-section, i.e., the function that gives the probability of scattering at any given angle, is known, being dependent on the atomic number of the scattering atom. FIG. 4 depicts the method to be used for such depth information. Assuming a known body composition, the angular dependent scattering cross section is a known function. Consequently, assuming, as in FIG. 4, a photon propagating along direction 510, if this photon is scattered at point 520, the energy of the scattered photon will be deposited at point 520a, while if the same photon were scattered at point 530, the energy would be deposited at point 530a. Since the energy detector of this invention is capable of determining the distance 540 and 550, indicated in FIG. 4, it follows that the scattering angle is known, and with it the distance, away from the energy detector array, of the scattering center. This ramification can also be used in conjunction with CAT scans, therefore decreasing the total radiation dose needed for them.

Various modifications and enhancements can be made to the embodiments disclosed herein without departing from the spirit and scope of the present invention.

We claim:

1. A radiation imaging system for producing images of a scanned object comprising:

a radiation source for applying, to at least one point of the object, a collimated radiation beam extending in an incident direction;

detector means for producing a first electrical signal having a first value representing the energy of the portion of said beam that transmits through the object along the incident direction and a second electrical signal representing the energy of the scattered portion of said beam scattered from the incident direction by the object;

information processing means for receiving said first and second electrical signals and displaying a visual representation of the point of the object by using a combination of the information content of said first and second electrical signals;

a scanner assembly for moving said beam in a scanning pattern throughout a surface zone of the object and said source applying said beam intermittently throughout the surface zone and said detector means producing first and second electrical signals for each point representing respectively the energy level of the incident beam transmitted portion and energy level of the scattered beam portion;

wherein said detection means comprises a detector array of individual detectors arranged generally in a plane oriented generally perpendicular to the incident direction of said beam and a positioning means for maintaining the more centrally located detectors at a position to intercept the beam incident direction as the scanner moves the incident beam in a scanning pattern;

wherein said first electrical signal has a value representative of the outputs of the more centrally located detectors and said second signal has a value representative of the combined outputs of the other than centrally located detectors; and wherein said more centrally located detectors have a smaller detection area than that of said other than centrally located detectors.

2. A system according to claim 1, wherein said processing means receives a series of said first signals representing energy levels of the intermittent incident beam segments applied to the center most located detectors for converting said first electrical signals to a first series of digital representations of said series of first electrical signals, and wherein said processing means receives a series of second electrical signals representing the energy levels of the intermittently scattered beam segments applied to the other than center most located detectors for converting said second electrical signals to a second series of digital representations of said series of second electrical signals, and said processing means uses both said first and second series of digital representations to display an image of the scanned zone of the object.

3. A system according to claim 2, wherein said processing means generates and stores first array information representing an incident image using said first series of digital representations and generates and stores second array information representing a scattered image using said second series of digital representations.

4. A system according to claim 3, wherein said processing means combines said first and second stored array information for corresponding points of the object to produce a displayed image.

5. A system according to claim 4, wherein said second stored array information comprises information related to the distance from the point of the beam scatter to the detector plane taken along the beam incident line.

6. A system according to claim 1, wherein said radiation source comprises a low energy beam source.

* * * * *